US008882701B2

(12) United States Patent
DeBelser et al.

(10) Patent No.: US 8,882,701 B2
(45) Date of Patent: Nov. 11, 2014

(54) ADVANCED STEP THERAPY DELIVERY FOR AN AMBULATORY INFUSION PUMP AND SYSTEM

(75) Inventors: David DeBelser, Plymouth, MN (US); Clinton Robert Hetchler, Minnetonka, MN (US); David Pardee Sours, North Saint Paul, MN (US); Michael Wade Kersch, Saint Michael, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 108 days.

(21) Appl. No.: 12/631,076

(22) Filed: Dec. 4, 2009

(65) Prior Publication Data

US 2011/0137239 A1 Jun. 9, 2011

(51) Int. Cl.
*A61M 31/00* (2006.01)

(52) U.S. Cl.
USPC .............................. 604/65; 604/67; 604/151

(58) Field of Classification Search
USPC ............................................. 604/67, 65, 151
See application file for complete search history.

(56) References Cited

U.S. PATENT DOCUMENTS

| 5,000,664 A | 3/1991 | Lawless et al. |
| 5,181,910 A | 1/1993 | Scanlon |
| 5,219,330 A | 6/1993 | Bollish |
| 5,338,157 A | 8/1994 | Blomquist |
| 5,368,562 A | 11/1994 | Blomquist et al. |
| 5,389,078 A | 2/1995 | Zalesky et al. |
| 5,485,408 A | 1/1996 | Blomquist |
| 5,569,186 A | 10/1996 | Lord et al. |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,681,285 A | 10/1997 | Ford et al. |
| 5,695,473 A | 12/1997 | Olsen |
| 5,713,856 A * | 2/1998 | Eggers et al. ................... 604/65 |
| 5,782,805 A * | 7/1998 | Meinzer et al. ............... 604/131 |
| 5,810,771 A | 9/1998 | Blomquist |
| 5,822,715 A | 10/1998 | Worthington et al. |
| 5,876,370 A | 3/1999 | Blomquist |

(Continued)

FOREIGN PATENT DOCUMENTS

| EP | 1571582 | 9/2005 |
| JP | 200634323 | 2/2006 |

(Continued)

OTHER PUBLICATIONS

U.S. Appl. No. 11/523,794, filed Sep. 18, 2006; Inventor: Moubayed.

(Continued)

*Primary Examiner* — Laura Bouchelle
(74) *Attorney, Agent, or Firm* — Patterson Thuente Pedersen, P.A.

(57) ABSTRACT

Embodiments relate to systems, methods and devices for delivering a drug or other therapy to a patient with an ambulatory infusion pump configured to provide a series of tolerance-building steps leading up to a plateau delivery rate. The plateau delivery rate is maintained until the prescribed amount of drug or therapy fluid is delivered to the patient. Embodiments of the invention include providing the patient or other user with a mechanism to decrease, or step down, the therapy delivery rate if a tolerance was not achieved at a lower rate, and providing notifications prior to a step up in a dosage delivery rate.

24 Claims, 10 Drawing Sheets

(56) References Cited

U.S. PATENT DOCUMENTS

| | | | |
|---|---|---|---|
| 5,879,143 A | 3/1999 | Cote et al. |
| 5,935,099 A | 8/1999 | Peterson et al. |
| 5,935,106 A | 8/1999 | Olsen |
| 6,024,539 A | 2/2000 | Blomquist |
| 6,077,055 A | 6/2000 | Vilks |
| 6,241,704 B1 | 6/2001 | Peterson et al. |
| 6,248,057 B1 | 6/2001 | Mavity et al. |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,641,533 B2 | 11/2003 | Causey, III et al. |
| 6,744,350 B2 | 6/2004 | Blomquist |
| 6,773,412 B2 | 8/2004 | O'Mahony |
| 6,809,653 B1 | 10/2004 | Mann et al. |
| 6,852,104 B2 | 2/2005 | Blomquist |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,179,226 B2 | 2/2007 | Crothall et al. |
| 7,231,263 B2 | 6/2007 | Choi |
| 7,267,665 B2 | 9/2007 | Steil et al. |
| 7,278,983 B2 | 10/2007 | Ireland et al. |
| 7,291,107 B2 | 11/2007 | Hellwig et al. |
| 7,307,245 B2 | 12/2007 | Faries et al. |
| 7,324,012 B2 | 1/2008 | Mann et al. |
| 7,404,796 B2 | 7/2008 | Ginsberg |
| 7,471,994 B2 | 12/2008 | Ford et al. |
| 7,553,281 B2 | 6/2009 | Hellwig et al. |
| 7,734,323 B2 | 6/2010 | Blomquist et al. |
| 7,751,907 B2 | 7/2010 | Blomquist |
| 7,806,886 B2 | 10/2010 | Kanderian et al. |
| 7,869,851 B2 | 1/2011 | Hellwig et al. |
| 8,204,729 B2 | 6/2012 | Sher |
| 8,208,984 B2 | 6/2012 | Blomquist et al. |
| 8,219,222 B2 | 7/2012 | Blomquist |
| 8,221,345 B2 | 7/2012 | Blomquist |
| 2001/0031944 A1 | 10/2001 | Peterson et al. |
| 2001/0037217 A1 | 11/2001 | Abensour et al. |
| 2002/0072932 A1 | 6/2002 | Swamy |
| 2002/0077852 A1 | 6/2002 | Ford et al. |
| 2002/0143580 A1 | 10/2002 | Bristol et al. |
| 2002/0183693 A1 | 12/2002 | Peterson et al. |
| 2003/0032867 A1 | 2/2003 | Crothall et al. |
| 2003/0050621 A1 | 3/2003 | Lebel et al. |
| 2003/0060765 A1 | 3/2003 | Campbell et al. |
| 2003/0114836 A1 | 6/2003 | Estes et al. |
| 2003/0160683 A1 | 8/2003 | Blomquist |
| 2003/0163090 A1 | 8/2003 | Blomquist et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2004/0073095 A1 | 4/2004 | Causey, III et al. |
| 2004/0115067 A1 | 6/2004 | Rush et al. |
| 2004/0180810 A1 | 9/2004 | Pilarski |
| 2004/0225252 A1 | 11/2004 | Gillespie, Jr. et al. |
| 2004/0254434 A1 | 12/2004 | Goodnow et al. |
| 2005/0022274 A1 | 1/2005 | Campbell et al. |
| 2005/0030164 A1 | 2/2005 | Blomquist |
| 2005/0050621 A1 | 3/2005 | Thomas |
| 2005/0065760 A1 | 3/2005 | Murtfeldt et al. |
| 2005/0143864 A1 | 6/2005 | Blomquist |
| 2005/0171513 A1 | 8/2005 | Mann et al. |
| 2005/0197553 A1 | 9/2005 | Cooper |
| 2005/0197621 A1 | 9/2005 | Poulsen et al. |
| 2005/0272640 A1 | 12/2005 | Doyle et al. |
| 2005/0277872 A1 | 12/2005 | Colby et al. |
| 2006/0001550 A1 | 1/2006 | Mann et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0085223 A1 | 4/2006 | Anderson |
| 2006/0132292 A1 | 6/2006 | Blomquist |
| 2006/0167345 A1 | 7/2006 | Vespasiani |
| 2006/0202859 A1 | 9/2006 | Mastrototaro et al. |
| 2006/0253097 A1 | 11/2006 | Braig et al. |
| 2006/0276771 A1 | 12/2006 | Galley et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0083152 A1 | 4/2007 | Williams, Jr. |
| 2007/0093786 A1 | 4/2007 | Goldsmith et al. |
| 2007/0100222 A1 | 5/2007 | Mastrototaro et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0213657 A1 | 9/2007 | Jennewine et al. |
| 2007/0287985 A1 | 12/2007 | Estes |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0065007 A1 | 3/2008 | Peterson |
| 2008/0065016 A1 | 3/2008 | Peterson |
| 2008/0071209 A1* | 3/2008 | Moubayed et al. ............ 604/67 |
| 2008/0071210 A1 | 3/2008 | Moubayed |
| 2008/0071217 A1 | 3/2008 | Moubayed |
| 2008/0071251 A1 | 3/2008 | Moubayed |
| 2008/0097289 A1 | 4/2008 | Steil et al. |
| 2008/0106431 A1 | 5/2008 | Blomquist |
| 2008/0114299 A1 | 5/2008 | Damgaard-Sorensen |
| 2008/0132844 A1 | 6/2008 | Peterson |
| 2008/0139907 A1 | 6/2008 | Rao et al. |
| 2008/0147004 A1 | 6/2008 | Mann et al. |
| 2008/0171967 A1 | 7/2008 | Blomquist et al. |
| 2008/0172029 A1 | 7/2008 | Blomquist |
| 2008/0172031 A1 | 7/2008 | Blomquist |
| 2008/0177165 A1 | 7/2008 | Blomquist et al. |
| 2008/0206799 A1 | 8/2008 | Blomquist et al. |
| 2008/0228056 A1 | 9/2008 | Blomquist et al. |
| 2008/0269585 A1 | 10/2008 | Ginsberg |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2009/0093756 A1 | 4/2009 | Minaie |
| 2009/0212966 A1 | 8/2009 | Panduro |
| 2009/0247931 A1 | 10/2009 | Damgaard-Sorensen |
| 2010/0222765 A1 | 9/2010 | Blomquist et al. |
| 2010/0274751 A1 | 10/2010 | Blomquist |
| 2010/0324382 A1 | 12/2010 | Cantwell et al. |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0245524 A1 | 9/2012 | Estes et al. |
| 2012/0265722 A1 | 10/2012 | Blomquist |

FOREIGN PATENT DOCUMENTS

| | | |
|---|---|---|
| WO | WO0045696 | 8/2000 |
| WO | WO0152727 | 7/2001 |
| WO | WO02062212 | 8/2002 |
| WO | WO2005046559 | 5/2005 |
| WO | WO2007056592 | 5/2007 |
| WO | WO2008091320 | 7/2008 |
| WO | WO2008153689 | 12/2008 |
| WO | WO2008153819 | 12/2008 |

OTHER PUBLICATIONS

International Search Report and Written Opinion for International Application No. PCT/US2007/024424 dated Mar. 6, 2009.

(56) References Cited

OTHER PUBLICATIONS

European Office Action for European Application No. 08767734.6 Mailed Apr. 7, 2010.
European Office Action for European Application No. 08779626.4 dated May 25, 2010.
International Search Report and Written Opinion for International Application No. PCT/US2008/006801 dated Oct. 30, 2008.
International Search Report and Written Opinion for International Application No. PCT/US2008/006449 dated Oct. 10, 2008.
"Deltec Cozmo. Personalized Insulin Pump. Starting Guide"., http://web.archive.org/web/20041207133233/http://www.cozmore.com/Library/upload/starting_guide_032004/pdf>, Dec. 7, 2004. pp. 1-83.
Wikipedia's definition for "Basal Rate", 1 page. Printed on Jun. 12, 2009.
Compare Insulin Pump for Diabetes, 4 pages. www.diabetesnet.com., Jun. 18, 2009.
Walsh et al., "Pumping Insulin: Everything you need for Success on a Smart insulin Pump", Torrey Pines Press, San Diego. 2006.
Application and File History for U.S. Appl. No. 11/753,420, filed May 24, 2007, inventor Blomquist.
Application and File History for U.S. Appl. No. 12/774,991, filed May 6, 2010, inventor Blomquist.
Application and File History for U.S. Appl. No. 13/530,404, filed Jun. 22, 2012, inventor Blomquist.
Application and File History for U.S. Appl. No. 11/755,480, filed May 30, 2007, inventor Blomquist.
Application and File History for U.S. Appl. No. 13/465,570, filed May 7, 2012, inventor Blomquist.
Application and File History for U.S. Appl. No. 11/626,653, filed Jan. 24, 2007, inventors Blomquist et al.
Application and File History for U.S. Appl. No. 12/720,306, filed Mar. 9, 2010, inventors Blomquist et al.
Canadian Office Action for Canadian Application No. 2,782,673 dated Sep. 10, 2013.
IPRP and Written Opinion for International Application No. PCT/US2010/056226 dated Jun. 14, 2012.
Japanese Office Action for Japanese Application No. 2012542037 dated Sep. 2, 2014. English Translation Not Available.

\* cited by examiner

ADVANCED STEP THERAPY DELIVERY FOR AN AMBULATORY INFUSION PUMP AND SYSTEM

TECHNICAL FIELD

The invention relates generally to ambulatory infusion pumps and more specifically to step therapy delivery by an ambulatory infusion pump.

BACKGROUND

Ambulatory infusion pumps are useful for providing a variety of drug therapies. Ambulatory pumps can be particularly beneficial for therapies which must be delivered over an extended period of time.

One such therapy is intravenous immunoglobulin (IVIG). IVIG is used primarily to treat immune deficiencies, inflammatory and autoimmune disorders, and acute infections. Patients receiving IVIG therapies typically need to build up a tolerance to the IVIG during delivery, meaning that IVIG is initially administered at a low rate and, as the infusion time progresses, the rate is gradually increased to a steady state or "plateau" rate that is maintained until the prescribed amount of IVIG has been delivered to the patient. IVIG is not the only therapy that utilizes this type of delivery profile.

While some conventional infusion pumps can accommodate such a delivery profile, setting up and programming the profiles on the pumps is complicated and time-consuming. Further, many conventional pumps use spreadsheet-based profiles that cannot be adjusted or customized, either prior to infusion to accommodate the needs of a particular patient or during infusion if a patient is not tolerating the delivered drug and needs to decrease the rate of infusion on demand.

SUMMARY OF THE INVENTION

Embodiments relate to systems, methods and devices for defining a step delivery function for an ambulatory infusion pump and delivering, by the pump, a drug according to the step delivery function.

In one embodiment, an ambulatory infusion pump comprises an infusion therapy delivery mechanism, a graphical user interface (GUI) configured to receive a plurality of parameters defining a step delivery function, the plurality of parameters comprising an initial rate, a plateau rate, a step duration, a rate increment and a total infusion volume, and a processor coupled to the therapy delivery mechanism and configured to calculate an infusion duration based on at least one of the plurality of parameters and to cause the therapy delivery mechanism to operate based on the step delivery function.

In one embodiment, a method of defining a step delivery function for an ambulatory infusion pump comprises receiving an initial rate, a plateau rate, a step duration, a rate increment and a total infusion volume, and automatically determining an infusion duration based on at least the initial rate, the plateau rate, the step duration, the rate increment and the total infusion volume.

In one embodiment, an infusion system comprises an initial rate setting, a plateau rate setting, a step duration setting, a rate increment setting, a total infusion volume setting, and an infusion duration setting that is automatically set according to the initial rate setting, the plateau setting, the step duration setting, the rate increment setting and the total infusion volume setting.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments of the invention relate to a step therapy delivery system for an ambulatory infusion system. In one embodiment, the ambulatory infusion system can be a CADD-Solis® Ambulatory Infusion System from Smiths Medical ASD, Inc. The ambulatory infusion system can also be of the type disclosed in commonly owned U.S. Patent Application Pub. Nos. 2008/0065007, 2008/0065016 and 2008/0132844, assigned to Smiths Medical ASD, Inc., which are incorporated by reference herein in their entireties. In other embodiments, other infusion pumps can be used.

Figure 1A:
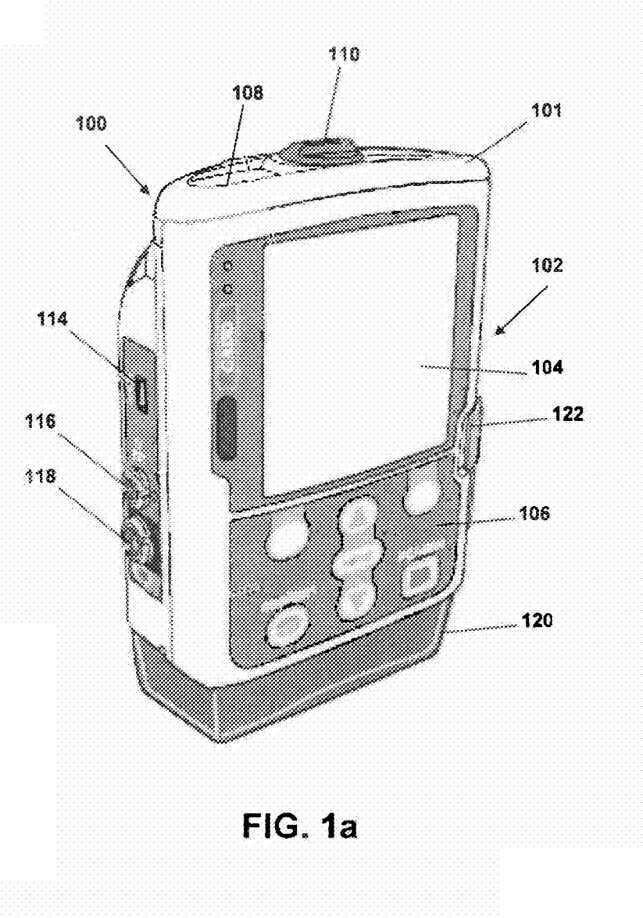
FIG. 1a is a front perspective view of an ambulatory infusion pump according to an embodiment.
Figure 1B:
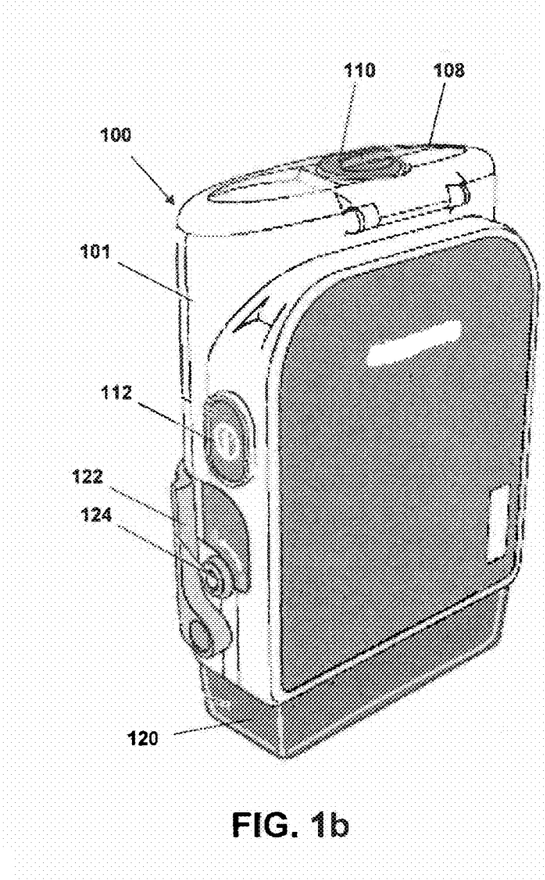
FIG. 1b is a rear perspective view of an ambulatory infusion pump according to an embodiment.
Figure 2:
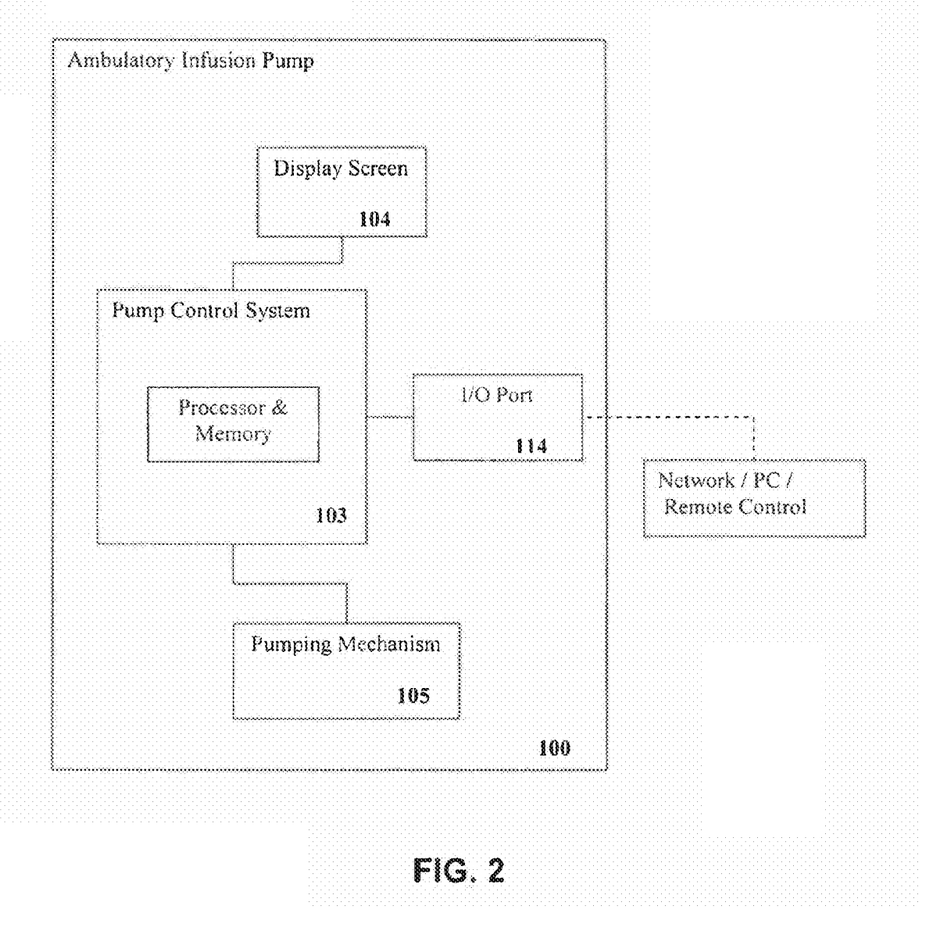
FIG. 2 is a block diagram of selected elements of ambulatory infusion pump of FIGS. 1a and 1b.

An exemplary ambulatory infusion pump 100 can provide a step delivery therapy to a patient and is depicted in FIGS. 1a and 1b, and FIG. 2. Ambulatory infusion pump 100 includes a pump control system 103 with a processor and memory programmable with selected protocols, profiles and other settings for controlling operation of a pumping mechanism 105. Ambulatory infusion pump 100 can also include a control module 101 for relaying commands to the control system 103. Control module 101 can include a user interface 102 having a display screen 104 and a control pad 106. Control module 101 can also include a battery door 108, including a knob 110 for locking and unlocking the door 108, which covers a battery compartment in which batteries for powering the pump 100 can be contained. Control module 101 can also include a power switch 112 for turning pump 100 off and on, a USB port 114, or other appropriate I/O interface, for connecting pump 100 to a computer having software designed to interface with pump 100, an AC power jack 116 for connecting an AC power cord for powering pump 100, and a remote dose cord jack 118 for connecting a remote dose cord that provides an alternative way to activate patient-controlled dosing.

Infusion pump 100 can further include a replaceable cassette 120 connected to control module 101. In one embodiment, cassette 120 includes a reservoir containing the medication that is to be delivered to the patient. Tubing can extend from the cassette 120 and communicate with an infusion set or catheter to deliver the medication to the patient. The control module 101 can be used to control the flow of medication from the cassette. One example of such a cassette is the CADD® Medication Cassette Reservoir from Smiths Medical ASD, Inc., though other cassettes can be used in other embodiments. In another embodiment, cassette 120 can include tubing that interfaces with a remote medication reservoir such as an IV bag. Tubing can extend from the reservoir to the cassette and then to an infusion set or catheter, and flow of medication through the tubing can be controlled with control module 101. One example of such a set is part of the CADD® Administration Set from Smiths Medical ASD, Inc.

A step delivery can be used with various drug therapies, though in one embodiment a step function for pump 100 is tailored for intravenous immunoglobulin (IVIG) therapies. IVIG therapies typically require a period of initial dosing. Once complete, an increased dosage (or "step up") can be periodically delivered. Step delivery allows the infusion of a drug at an initial rate with step increases to a plateau rate. If patient tolerance is not successful at any rate, the treatment can be scaled back or stopped on demand. Multiple steps down can be applied, reducing the dosage rate down to any previous rate. In other embodiments, a step delivery profile can be suitable for nutritional and other therapies.

Figure 3:
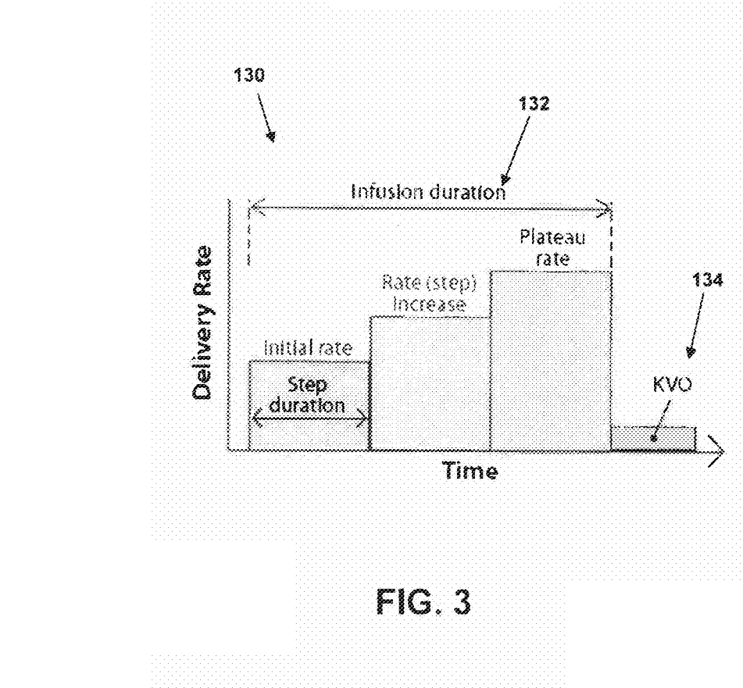
FIG. 3 is a graphical representation of the various parameters of therapy delivery according to an embodiment.

The step delivery profile of the pump 100 is selectively defined by parameters provided to the pump control system 103. In one embodiment: an initial rate, a plateau rate, a step duration, a rate (step) increase or increment, and a total infusion volume, as shown by diagram 130 depicted in FIG. 3 can be provided. An additional parameter, infusion duration 132, does not have to be provided by a user in an embodiment; rather, infusion duration 132 is automatically calculated based upon one or more of the other parameters in an embodiment. For example, a minimum programmable infusion duration is defined by a combination of the infusion volume, step duration and various rates of delivery. In an embodiment, pump 100 provides a calculated infusion duration 132 after the other parameters are programmed. In an embodiment, pump control system 103 also calculates the total number of steps necessary to transition from the initial rate to the plateau rate based on one or more programmed parameters. During delivery of a step delivery profile, a user may "step down" a delivery rate. In one embodiment, pump 100 automatically adjusts one or more parameters of the programmed step delivery profile to accommodate the departure from the initial program. This can include adjusting, i.e., lengthening, the total infusion duration automatically. In an additional embodiment, an optional KVO ("keep vein open") rate 134 is provided, which allows delivery of a minimal amount of drug to help maintain catheter patency. The KVO rate 134 can be considered by the pump 100 in determining a calculated infusion duration 132 in one embodiment. Thus, in various embodiments, the step calculation function of the pump control system 103 calculates a single total infusion duration 132 based on the entered parameters and therefore does not need minimum and maximum duration parameters.

Figure 4:
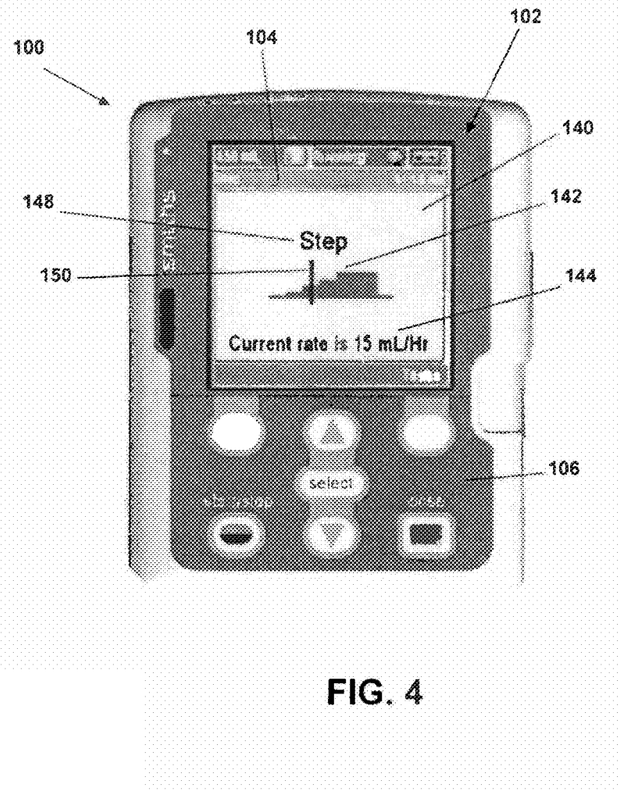
FIG. 4 is a view of a delivery profile graphic provided by a ambulatory infusion pump graphical user interface (GUI) according to an embodiment.

As depicted in FIG. 4, the display screen 104 of the pump 100 provides a graphical user interface (GUI) 140 during operation. An example delivery profile graphic 142 when the pump 100 is started is shown on the display screen 104. The information displayed on the GUI 140 may vary but can include information of most interest to a user or patient during delivery, such as the current rate of delivery 144, the mode of operation 148, and any other appropriate status indications. In the embodiment of FIG. 4, the pump 100 is in step mode 148. During infusion, the GUI 140 can present an indicator graphic 150, along with the delivery profile graphic 142, illustrating how far the patient's treatment has progressed. In the example shown, the therapy delivery is in the second of four stages, at a rate of fifteen mL per hour.

Figure 5:
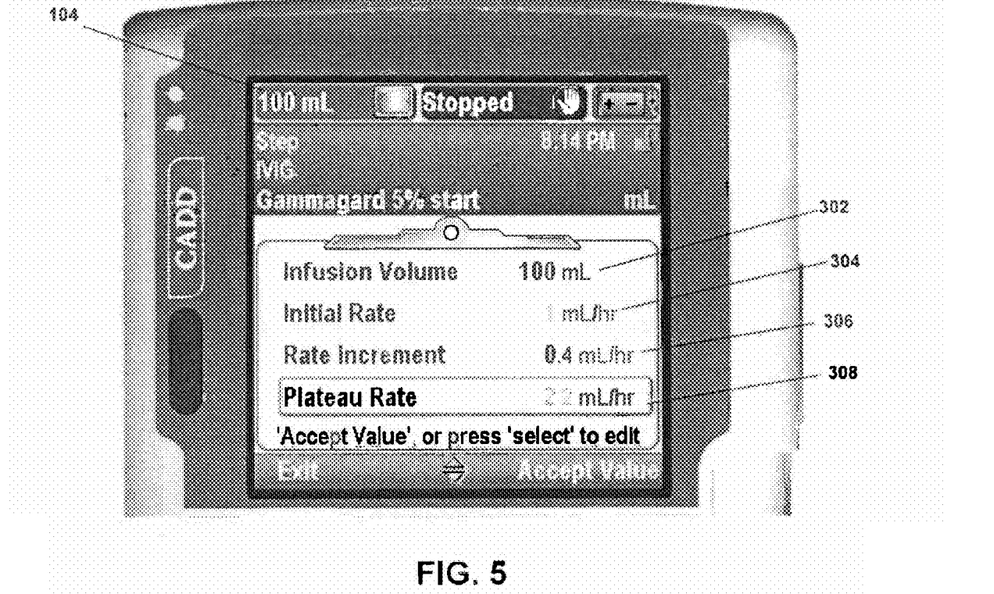
FIG. 5 is a view of a menu provided by a GUI according to an embodiment.
Figure 6:
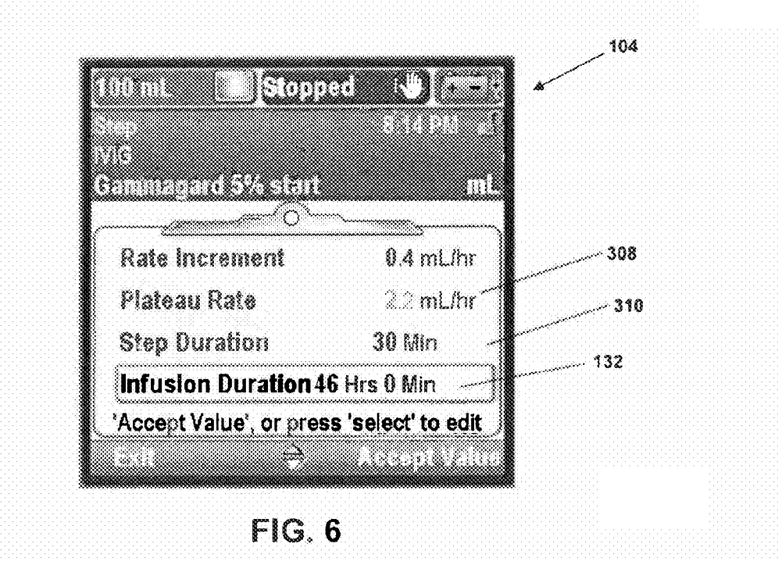
FIG. 6 is a view of a menu provided by a GUI according to an embodiment.
Figure 7:
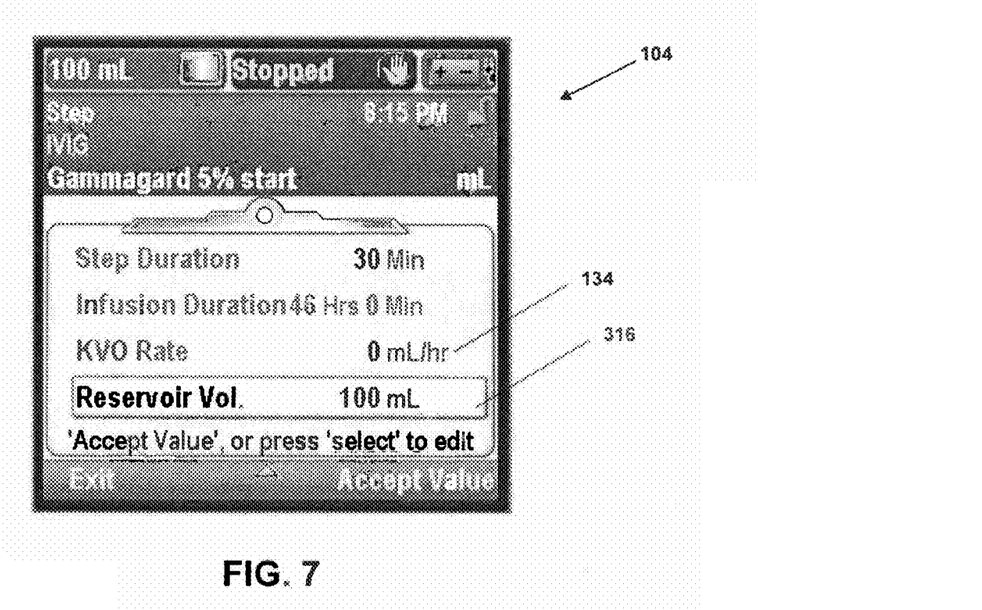
FIG. 7 is a view of a menu provided by a GUI according to an embodiment.

As depicted in FIGS. 5-7, programming screens present a user with an interface to input the parameters defining the therapy delivery. The user, potentially a clinician or home health-care provider, can enter the dosage parameters provided by a prescribing physician. The user can also utilize the interface to determine the status of treatment and reduce the dosage rate if necessary. In one embodiment, certain parameters or profiles specific to a patient can be retained or stored by pump 100, or by a related computer system, to facilitate quicker, more convenient, and safer use of pump 100; in particular to avoid programming errors or delivery of a profile intended for another patient. In other embodiments, individual or multiple profiles can be programmed using a related computer system and software, and then downloaded to one or more pumps 100 for patient therapy.

FIG. 5 depicts a programmed infusion volume 302 of one hundred mL. Infusion volume 302 is the total volume of drug or therapy fluid to be delivered according to a prescription. Entering a new infusion volume 302 resets the configured infusion profile so that therapy delivery starts at the beginning of a new infusion duration 132 for the patient.

Initial Rate 304 is the rate at which therapy delivery will begin. This also can be the minimum delivery rate that a user can "step down" to. Rate Increment 306 is the amount of desired amount of medication delivery increase for each step.

Plateau Rate 308 is the maximum rate at which the pump 100 is to deliver the medication. The pump 100 begins at the initial rate, and increases by the rate increment until the plateau rate 308 is reached, absent a step-down indication from a user. The pump 100 can run at this rate until the reservoir volume reaches zero or when the predetermined infusion volume 302 is delivered. The pump control system 103 can calculate the rate of delivery that will occur during the plateau portion of the infusion profile based on the infusion volume and infusion duration, depending on the desired parameters. The pump 100 can be pre-configured with a maximum allowable rate. For example, a rate above 250 mL/hr can require a high volume therapy administration set.

A low volume therapy administration set would not accept parameters that resulted in a plateau rate 308 above 250 mL/hr.

Step Duration 310 is the length of time programmed for each step during medication delivery. This time period corresponds to the duration of each step's therapy delivery period. The sum of all step duration 310 periods for each step required to reach the plateau rate 308, as well as the length of the plateau period, is then equal to the total infusion duration 132 to deliver the full infusion volume 302.

Infusion duration 132 is the time required to deliver the total infusion volume 302. In an embodiment, infusion duration 132 is calculated by the pump 100 based on one or more of the initial values programmed for the patient-specific parameters: infusion volume 302, initial rate 304, rate increment 306, plateau rate 308, and step duration 310. The user does not need to provide a duration value in one embodiment. Once the parameters are entered, the pump control system 103 calculates infusion duration 132.

Reservoir Vol. 316 is the volume of fluid contained in the reservoir or cassette 120. The administrator can configure a standard reservoir volume 316 which allows the reservoir volume 316 setting to be quickly reset to that configured value. As shown in FIG. 7, a clinician can adjust the reservoir volume 316 to another amount, resetting the reservoir volume. In one embodiment, the reservoir volume 316 cannot be set to less than the programmed infusion volume 302. The reservoir volume 316 value decreases as the pumping mechanism is primed or delivers fluid.

The KVO Rate, or "keep vein open" rate, 134 is optional. It allows delivery of a minimal amount of a drug to help maintain catheter patency. If a delayed start is programmed, the KVO rate 134 is active during the initial delay. It is also active after the infusion profile is complete if the reservoir volume 316 programmed is greater than the infusion volume 302. If a KVO delivery rate 134 is intended at the end of the infusion profile, the reservoir volume must be larger than the infusion volume so that automatic KVO delivery may occur. The KVO delivery rate 134 continues until the reservoir volume 316 reaches zero mL or until the pumping mechanism is stopped.

Figure 8:
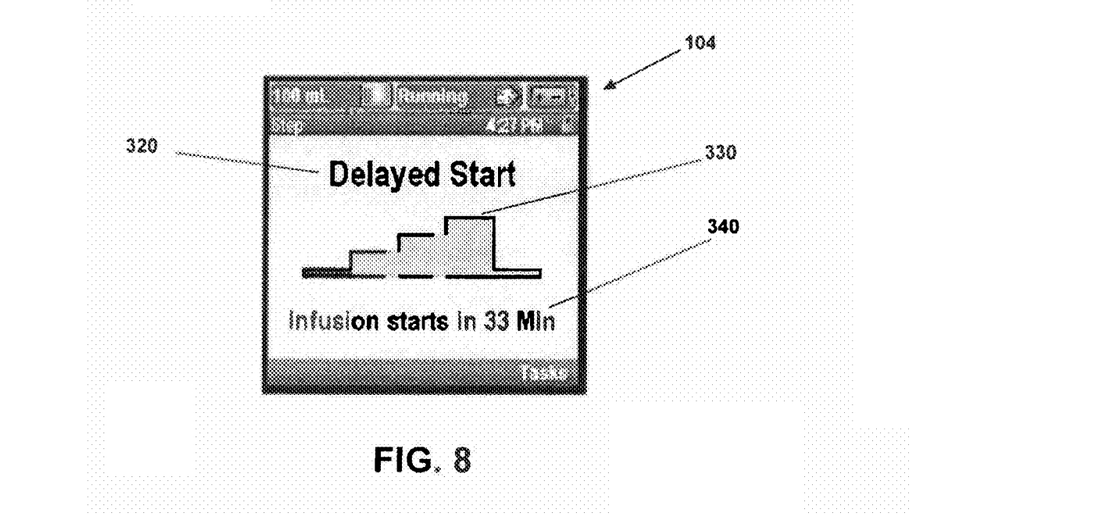
FIG. 8 is a view of a delayed start graphic provided by a GUI according to an embodiment.

The user can also program a delayed start time (not depicted) that is the time that the next infusion delivery will begin. It is displayed only if a delayed start is programmed. FIG. 8 depicts pump 100 in delayed start mode 320. The graphic 330 indicates that the pump 100 is in the first stage of minimum therapy delivery. The time 340 until the delivery of the therapy increases to the initial rate 304 is also displayed and periodically updated on display screen 104.

Figure 9:
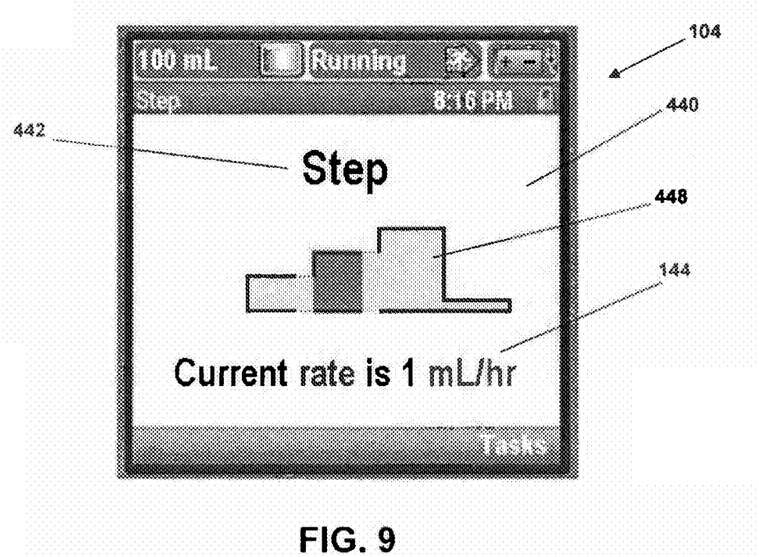
FIG. 9 is a view of a delivery profile graphic provided by a GUI according to an embodiment.
Figure 10:
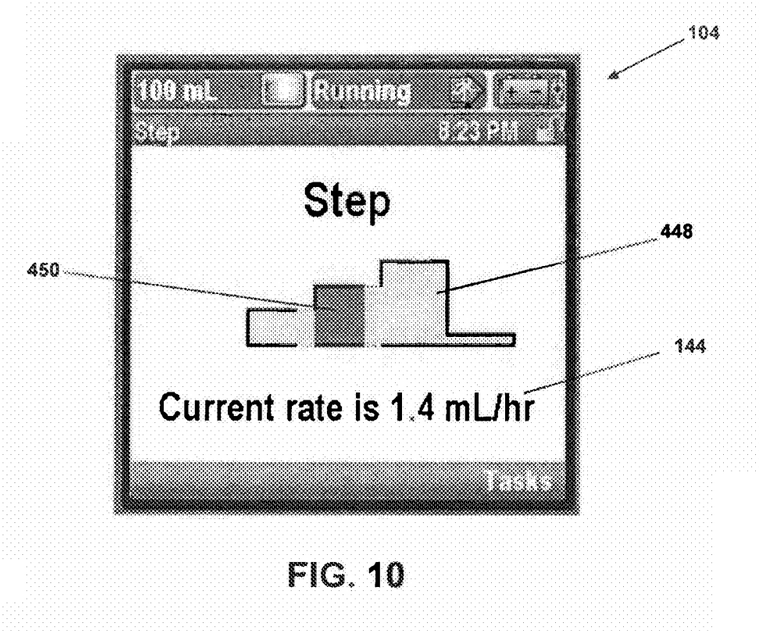
FIG. 10 is a view of a delivery profile graphic provided by a GUI according to an embodiment.

FIGS. 9 and 10 depict two examples of the display screen 104 of the pump 100 presenting a running status screen 440 indicating the current rate of delivery 144 and that the pump 100 is in the step mode 442 of operation. The running status screen 440 includes an example of a step delivery icon 448 that includes a status bar 450. The location of the status bar 450 in the middle of the delivery icon 448 indicates that the pump 100 is at an intermediate step in the therapy delivery. The pump 100 is delivering a medication at a current rate 144 that is less than the plateau rate 308.

Figure 11:
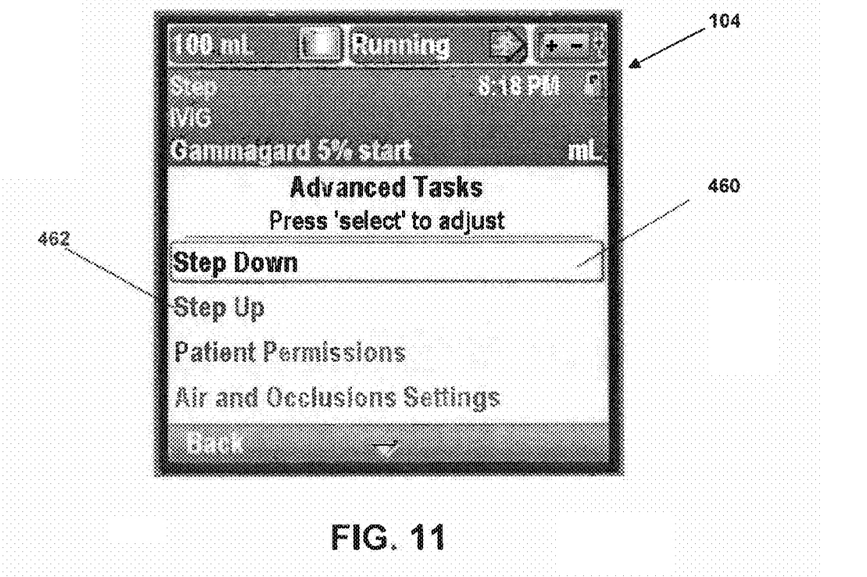
FIG. 11 is a view of a menu provided by a GUI according to an embodiment.

FIG. 11 depicts GUI menu commands Step Down 460 and Step Up 462 from the advanced tasks menu that can be used to change the actual current step, i.e. the infusion duration by reducing or increasing the rate of therapy administration. The step up and step down procedures are described below. After the selection of the Step Down 460 or Step Up 462 commands, the infusion duration time is automatically recalculated in one embodiment. The displayed total infusion duration 132 value can change to reflect the new setting, or it can be configured to display the initial time value and indicate that a change has been directed that deviated from the original configuration.

Figure 12A:
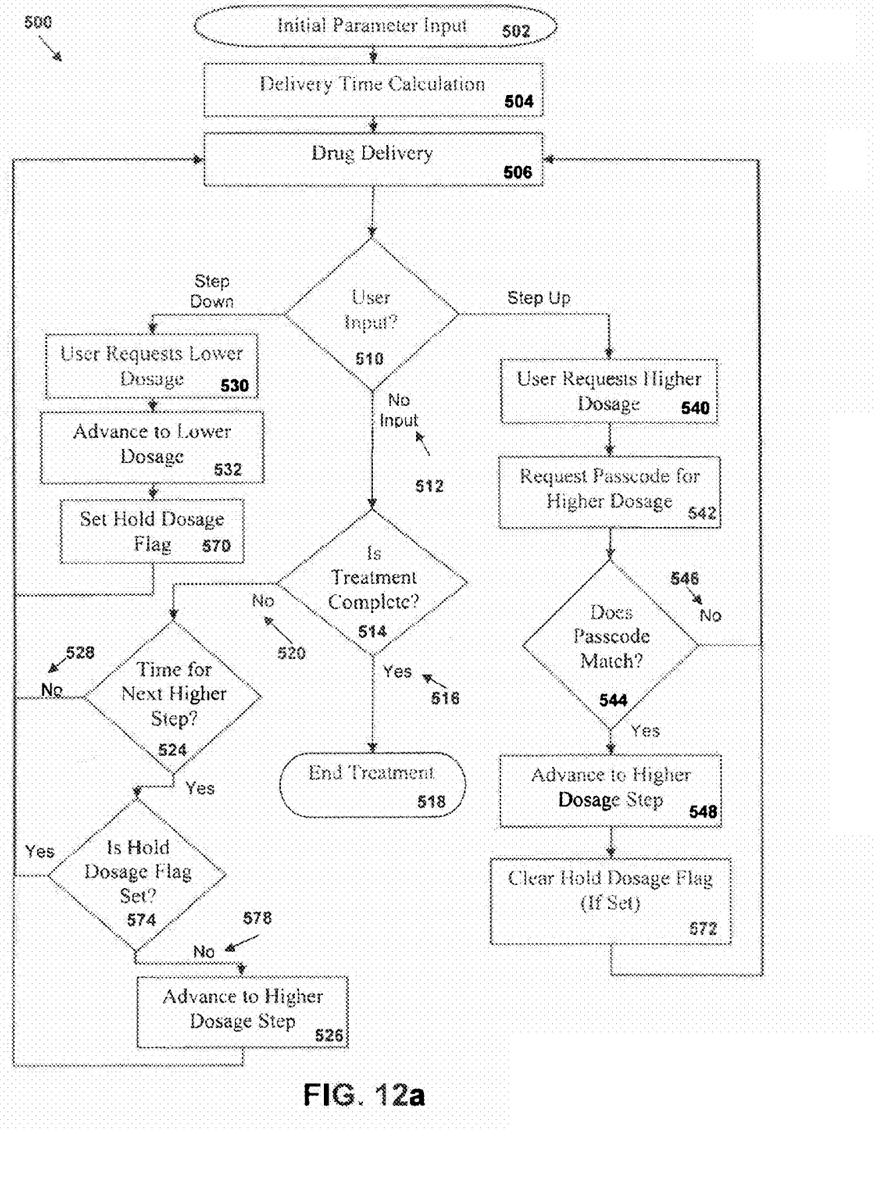
FIG. 12a is a flowchart of a step therapy delivery system according to an embodiment.
Figure 12B:
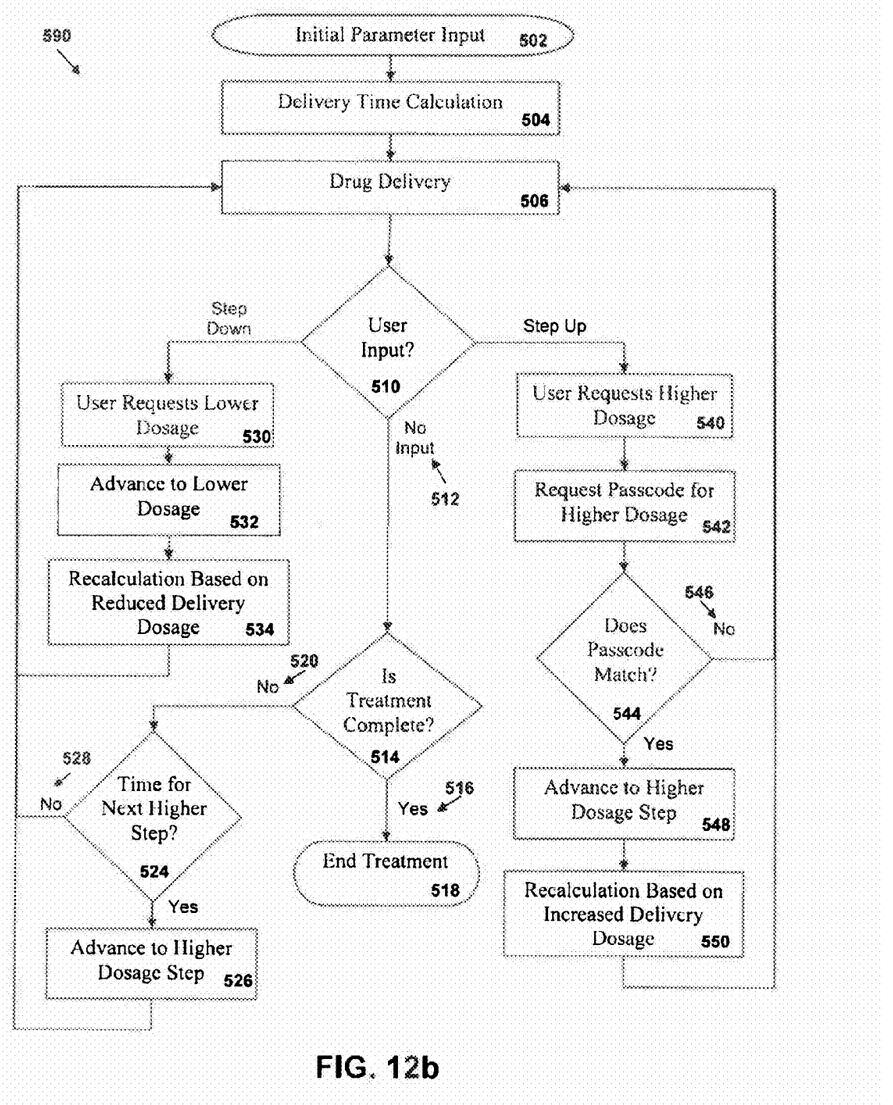
FIG. 12b is a flowchart of a step therapy delivery system according to an embodiment.

FIGS. 12a and 12b depict flowcharts 500 and 590 of exemplary embodiments of a step therapy protocol for an ambulatory infusion system. Initially, a clinician or health care provider inputs the desired parameters 502 as discussed above. Typical parameters can include total infusion volume, initial rate, rate increment, plateau rate, and step duration in an embodiment. The pump control system 103 will next calculate the initial infusion duration delivery time 504. Once the settings are confirmed by the user, the pump 100 can commence the delivery 506 by engaging the pumping mechanism of the pump 100.

The stepped delivery function of the pump 100 is interruptible, for example a patient may selectively hold at a current level rather than stepping up to the next level, or may step back to a previous lower therapy delivery level if tolerance was not achieved. During delivery, the pump 100 also provides patient convenience features, such as a notification at step up transition. The notification can come in advance of a transition such that a user can check the patient's vitals or condition prior to a transition.

The pump 100 can receive user input 510 through the GUI 140 during drug delivery 506. If there is no user input, the delivery mode 506 continues until the pump control system 103 determines that treatment is complete 516. The determination of completed treatment can be based on the delivery of the entered infusion volume 302. When the treatment is complete 520, the pumping mechanism can either be deactivated, or reduced to a KVO delivery rate 134 if configured and if reservoir volume 316 has not reached zero mL.

If treatment is not complete 520, the pump control system 103 will check to see if the step duration 310 time period has elapsed 524. If step duration 310 for the current therapy delivery period has been completed, the pump 100 will advance to the next higher dosage step 526 and increase the drug delivery 506 by the amount of the rate increment 306. The rate of drug delivery 506 is limited by the plateau rate 308. Optionally, the pump 100 can provide a notification at or before the dosage increase, or prompt the user for a confirmation to acknowledge the dosage increase before the higher dosage is delivered. The pump 100 can continue with drug delivery as before unless prompted by the user 510 or treatment is completed 516. If the step duration 310 has not elapsed 528, the pump 100 will continue with drug delivery 506.

If the user inputs a step down command requesting a lower dosage 530, then the pump 100 will reduce the therapy to the lower dosage 532 by the amount of one dosage rate increment 304. In the embodiment depicted in FIG. 12a, the pump 100 will remain at this lower drug delivery 506 stage unless requested by the user to provide a higher dosage 540 or until treatment is completed 516. The pump 100 can maintain the lower delivery rate by setting an internal hold dosage flag 570 that is checked 574 prior to advancing to a higher dosage step 526. In the embodiment of FIG. 12b, the reduction in dosage causes a recalculation 534 of the infusion duration 132 based on the new reduced delivery dosage by the pump control system 103. The user can enter multiple step down commands, reducing the dosage by one or more increments, or halting treatment completely. In an alternative embodiment, the pump 100 can prompt the user for permission to increase the dosage after another step duration 310 time period has elapsed.

If the user inputs a request for a higher dosage 540, the pump 100 can prompt the user to enter a passcode 542. The request for a passcode can be used to prevent the patient receiving treatment for increasing their dosage without supervision, or to limit the ability to increase the dosage to certain authorized individuals. Passcodes can also be used by default for any programming feature or in other situations related to the use of the pump 100. If a requested passcode does not match 546 the pump 100 remains at the current drug delivery 506 stage. If the preconfigured passcode is entered the pump 100 advances to the higher dosage stage 548 by the amount of one dosage rate increment 304. In the embodiment of FIG. 12b, the increase in dosage leads to a recalculation 550 of the infusion duration 132 based on the increased delivery dosage by the pump control system 103. In the embodiment of FIG. 12a, the hold dosage flag 570 can be cleared 572 if the user requests a higher dosage level 540. The user can enter multiple step up commands, increasing the dosage by one or more increments, up to the configured plateau rate. One skilled in the art will appreciate that other variations or combinations of the embodiments described in FIGS. 12a and 12b are possible.

Figure 13:
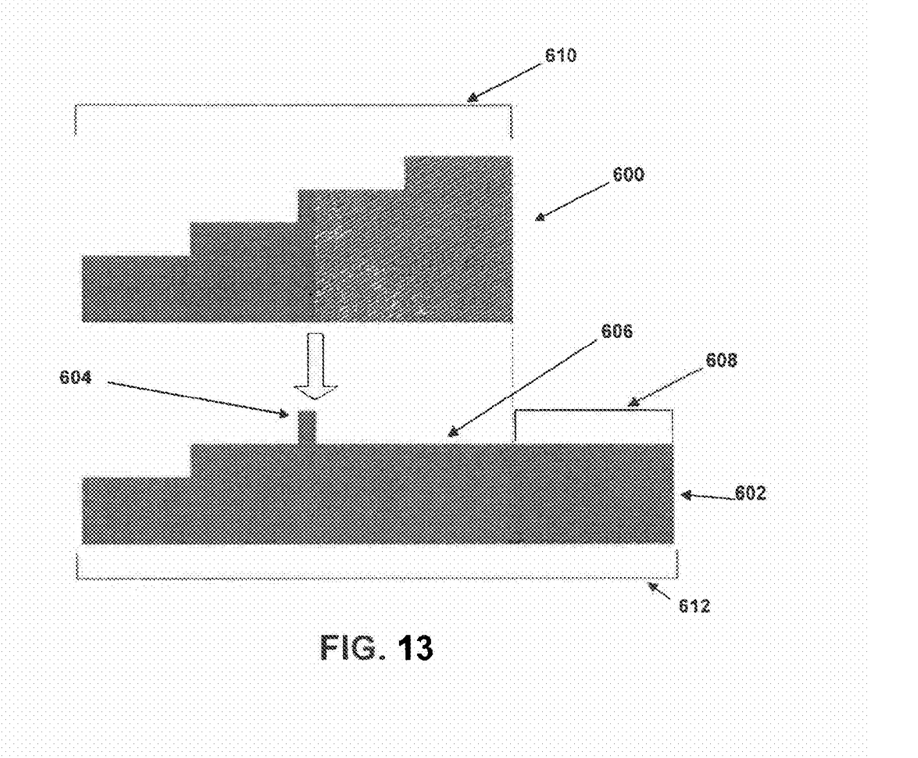
FIG. 13 is a graphical representation of therapy delivery of a directed "step down" according to an embodiment.

FIG. 13 depicts an example of an initial delivery profile 600 and a resulting delivery profile 602 after a decrease or "step down" in dosage rate. If the user experiences an adverse reaction to an increased dosage, the user can direct the pump 100 to revert back to the previous, lower, dosage level. As illustrated, the selection of the step down command option 460, on the GUI 140 of FIG. 11, decreases the therapy dosage from the current dosage 604 to the previous lower dosage 606. The decrease in dosage increases the overall therapy delivery time by an additional period 608. The additional period 608 extends the original dosage period 610 to the new dosage period 612. In this example, the previous lower dosage 606 rate is maintained for the entire new dosage period 612. No automatic increase in dosage is performed by the pump 100, though this can vary in other embodiments.

Figure 14:
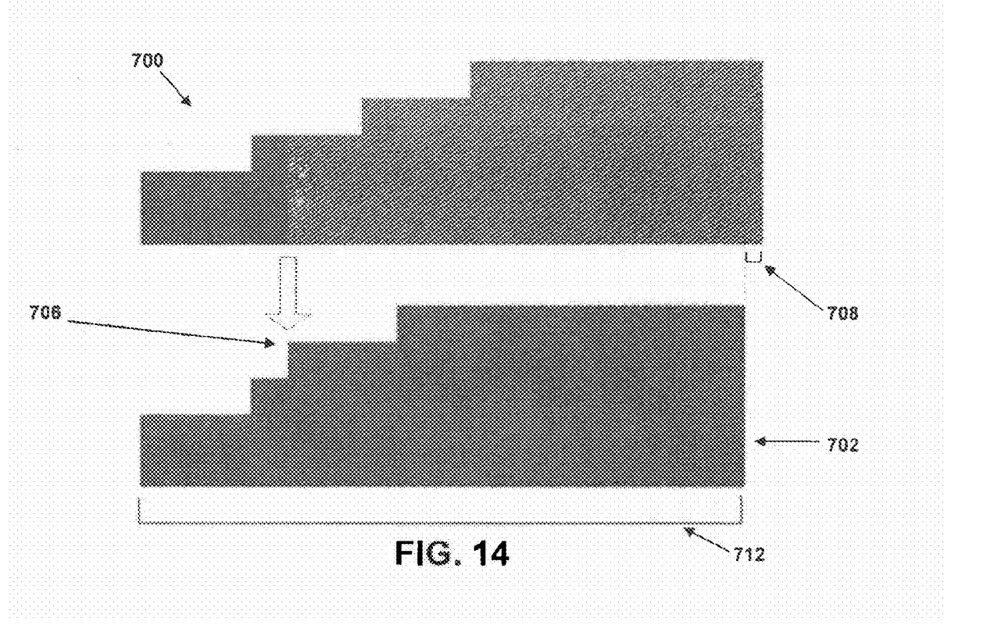
FIG. 14 is a graphical representation of therapy delivery of a directed "step up" according to an embodiment.

FIG. 14 depicts an example of an initial delivery profile 700 and a resulting delivery profile 702 after an increase or "step up" in the dosage rate. As illustrated, the step up command 462 on the GUI 140 of FIG. 11 increases the therapy dosage to the next higher dosage 706. This dosage then continues for one entire new step duration 310 regardless of how far into the current step duration 310 the pump 100 had progressed when the "step up" option was initiated. The increase in dosage rate can decrease the overall therapy delivery time by a shortened period 708. This reduces the overall therapy delivery time required to administer the full infusion volume 302.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An ambulatory infusion pump comprising:
    an infusion therapy delivery mechanism;
    a graphical user interface (GUI) configured to receive a plurality of parameters defining a step delivery function, the plurality of parameters comprising an initial rate, a plateau rate, a step duration, a rate increment and a total infusion volume; and
    a processor coupled to the therapy delivery mechanism and configured to calculate an initial infusion duration based on at least one of the plurality of parameters and to cause the therapy delivery mechanism to operate based on the step delivery function, wherein the processor is further configured to automatically calculate a new infusion duration necessary to deliver the total infusion volume if at least one of the plurality of parameters or another step delivery function parameter is changed.

2. The pump of claim 1, wherein the GUI presents an option during operation of the therapy delivery mechanism to increase a delivery rate by an amount of the rate increment.

3. The pump of claim 1, wherein the GUI presents an option during operation of the therapy delivery mechanism to decrease a delivery rate by an amount of the rate increment.

4. The pump of claim 3, wherein the processor is configured to calculate a new infusion duration if the delivery rate is decreased during operation of the therapy delivery mechanism.

5. The pump of claim 3, wherein the delivery rate after the decrease is maintained for a period of time needed for the infusion therapy delivery mechanism to deliver the total infusion volume.

6. The pump of claim 1, wherein the GUI is configured to receive at least one parameter defining a delivery function selected from the group consisting of: a patient-controlled analgesia (PCA) delivery function, a continuous delivery function, an intermittent delivery function, and a taper delivery function.

7. The pump of claim 1, wherein the step delivery function is for an intravenous immunoglobulin (IVIG) therapy.

8. The pump of claim 1, wherein the GUI is configured to display the initial infusion duration.

9. The pump of claim 1, wherein the processor is configured to calculate a total number of steps in the step delivery function based on at least one of the plurality of parameters.

10. The pump of claim 1, wherein the step delivery function is unlimited by a user-defined maximum infusion time parameter.

11. A method of defining a step delivery function for an ambulatory infusion system comprising:

receiving an initial rate, a plateau rate, a step duration, a rate increment and a total infusion volume;

automatically determining an initial infusion duration based on at least the initial rate, the plateau rate, the step duration, the rate increment and the total infusion volume; and automatically determining a new infusion duration if a change occurs in at least one of the initial rate, the plateau rate, the step duration, the rate increment, the total infusion volume or a current delivery rate.

12. The method of claim 11, further comprising:
receiving a delivery rate reduction request.

13. The method of claim 12, further comprising reducing a current delivery rate by an amount of the rate increment.

14. The method of claim 11, further comprising providing a prompt to enter the initial rate, the plateau rate, the step duration, the rate increment and the total infusion volume.

15. The method of claim 14, wherein receiving further comprises receiving the initial rate, the plateau rate, the step duration, the rate increment and the total infusion volume as user interface inputs.

16. The method of claim 11, further comprising displaying the infusion duration on a graphical user interface.

17. The method of claim 11, further comprising selecting the step delivery function from the group consisting of a patient-controlled analgesia (PCA) delivery function, a continuous delivery function, an intermittent delivery function, a taper delivery function, and a step delivery function.

18. The method of claim 17, wherein delivering a drug comprises delivering an intravenous immunoglobulin (IVIG) drug.

19. The method of claim 11, further comprising delivering a drug according to the step delivery function.

20. The method of claim 11, wherein automatically determining a new infusion duration further comprises automatically determining a new infusion duration that is unlimited by a user-defined maximum infusion duration.

21. An infusion system comprising:
an initial rate setting;
a plateau rate setting;
a step duration setting;
a rate increment setting;
a total infusion volume setting; and
an infusion duration setting that is automatically set according to the initial rate setting, the plateau setting, the step duration setting, the rate increment setting and the total infusion volume setting and is unlimited by a user-defined maximum infusion time setting.

22. The system of claim 21, further comprising an ambulatory infusion pump having a pumping mechanism operable to deliver a drug according to a step function defined by the initial rate setting, the plateau setting, the step duration setting, the rate increment setting, the total infusion volume setting and the infusion duration setting.

23. The system of claim 22, wherein the drug is an intravenous immunoglobulin (IVIG) drug.

24. The system of claim 22, wherein the pump comprises a notification system operable to provide a notification prior to a change in a delivery rate of the drug.

* * * * *